United States Patent [19]

Dean

[11] Patent Number: 5,030,236
[45] Date of Patent: Jul. 9, 1991

[54] APPARATUS FOR ENHANCING BIOINTEGRATION OF BONY AND ENDOPROSTHESIS STRUCTURES

[75] Inventor: David B. Dean, Dallas, Tex.

[73] Assignee: Intermedics Orthopedics, Inc., Austin, Tex.

[21] Appl. No.: 368,195

[22] Filed: Jun. 19, 1989

[51] Int. Cl.⁵ .............................................. A61F 2/28
[52] U.S. Cl. ...................................... 623/16; 623/18; 128/419 F; 433/201.1
[58] Field of Search ................ 623/16, 18; 128/419 F, 128/419 K, 784; 433/173, 201.1

[56] References Cited

U.S. PATENT DOCUMENTS

| | | | |
|---|---|---|---|
| 4,027,392 | 6/1977 | Sawyer et al. | 433/201.1 X |
| 4,175,565 | 11/1979 | Chiarinza et al. | 433/32 |
| 4,195,367 | 4/1980 | Kraus | 128/419 F X |
| 4,314,554 | 2/1982 | Greatbatch | 128/419 F X |
| 4,549,547 | 10/1985 | Brighton et al. | 128/419 F |
| 4,602,638 | 7/1986 | Adams | 128/419 F |

FOREIGN PATENT DOCUMENTS 3113898 10/1982 Fed. Rep. of Germany ........ 623/16

OTHER PUBLICATIONS

"Electrical Stimulation of Hard and Soft Tissues in Animal Models", by Black, Clinics in Plastic Surgery, vol. 12, No. 2, Apr. 1985, pp. 243-257.

Primary Examiner—Richard J. Apley
Assistant Examiner—Joe H. Cheng
Attorney, Agent, or Firm—John R. Merkling

[57] ABSTRACT

An invasive prosthesis device is disclosed which includes an electrical circuit having a cathode and an anode for mounting on opposing sides of body tissue requiring healing. The cathode is connected to a source of power for transmitting electrical stimulating signals to the anode as target. The invasive device includes a constant current circuit which may include either a battery source of power or a power source iductively coupled to the constant current source circuit. If the power source is inductively coupled to the constant current source a diode rectifier can be coupled between the inductive coil and constant current source for rectifying the induced ac to dc. The prosthesis device includes a porous surface area located to maximize the bonding strength between the device and the body tissue. The cathode is located in the porous area and powered to limit tissue growth to ingrowth substantially within the porous area only. The constant current circuitry including the induction coil and time constant circuit or battery as appropriate are housed within the interior of the prosthesis device together with the leads interconnecting the constant current source to the cathode.

8 Claims, 7 Drawing Sheets

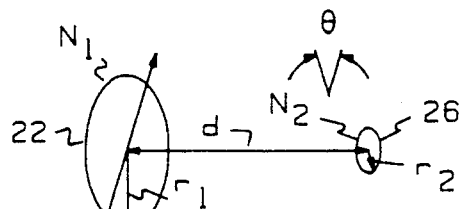
FIG. 1
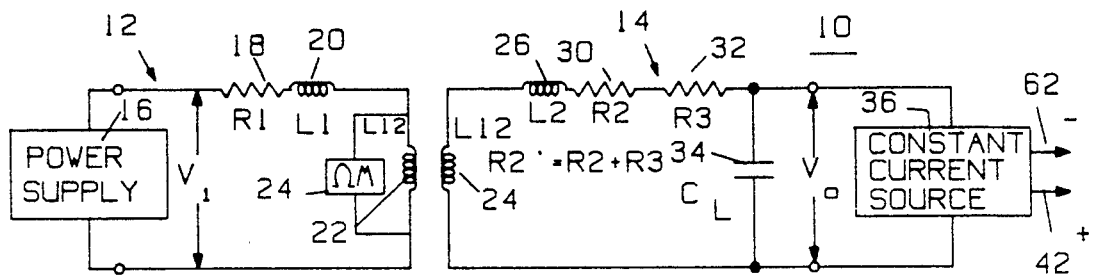
FIG. 2
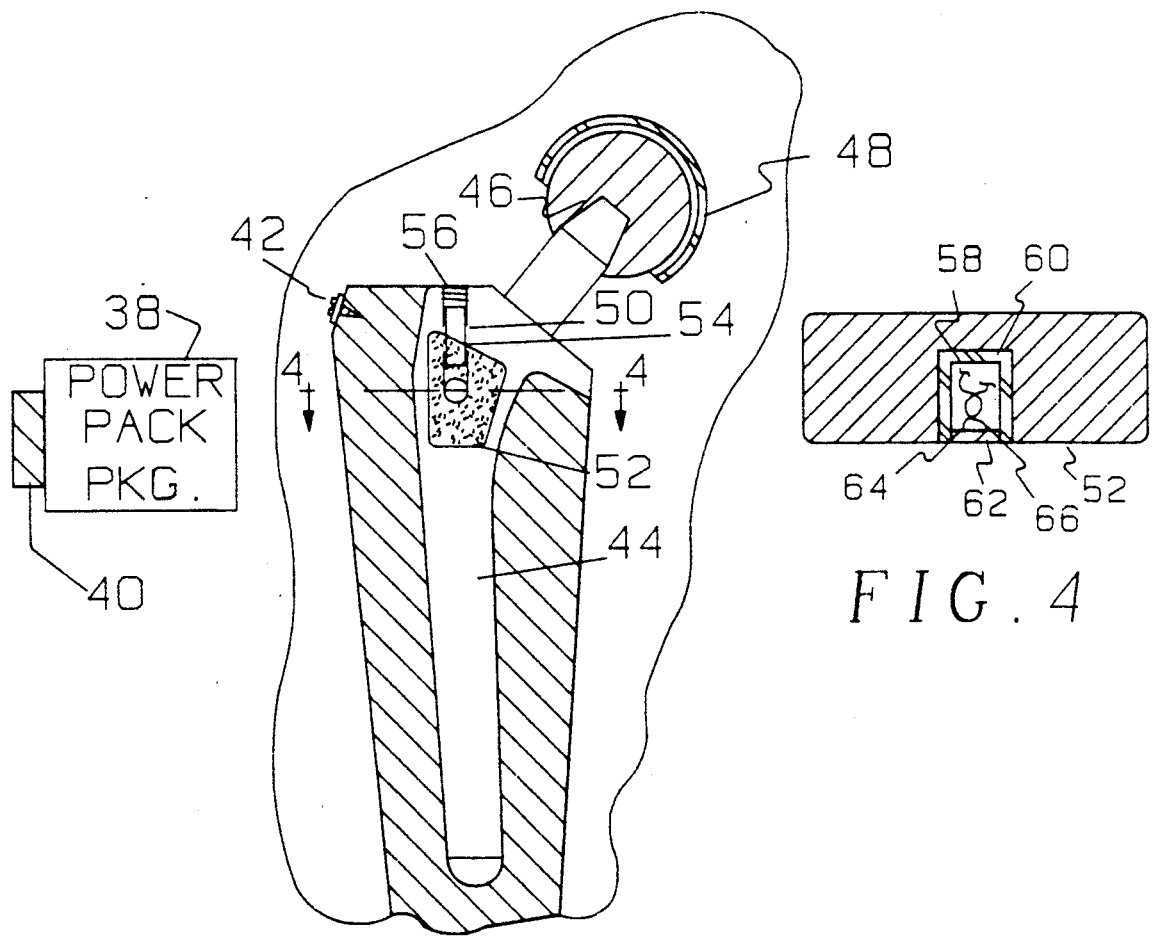
FIG. 3
FIG. 4

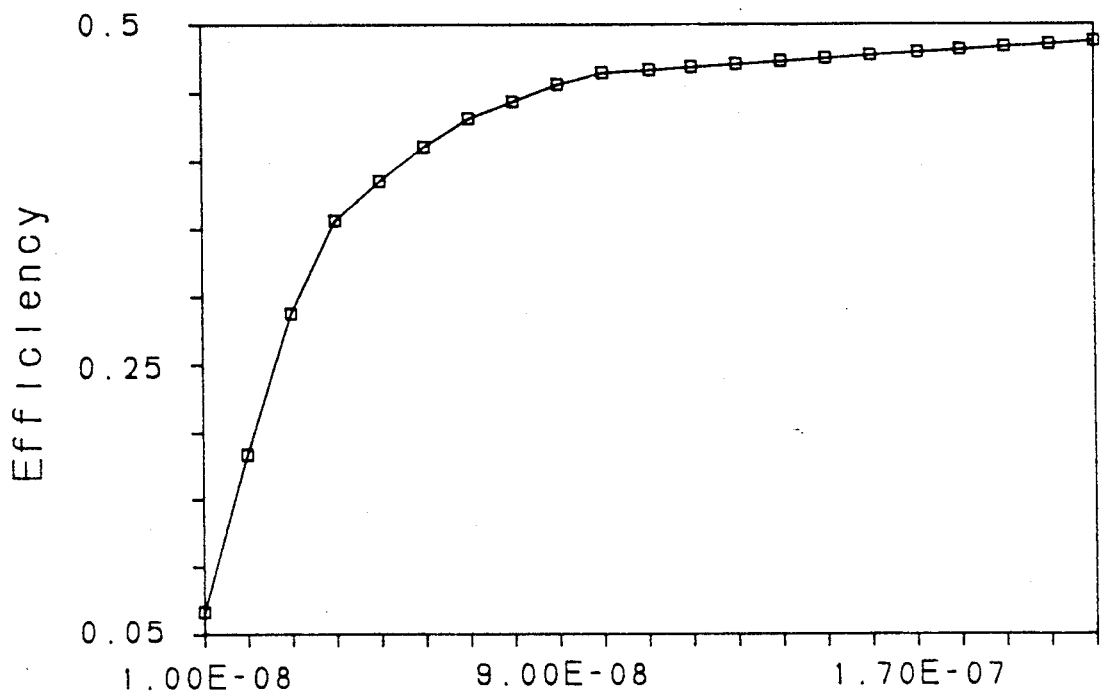
FIG. 13  Mutual Inductance
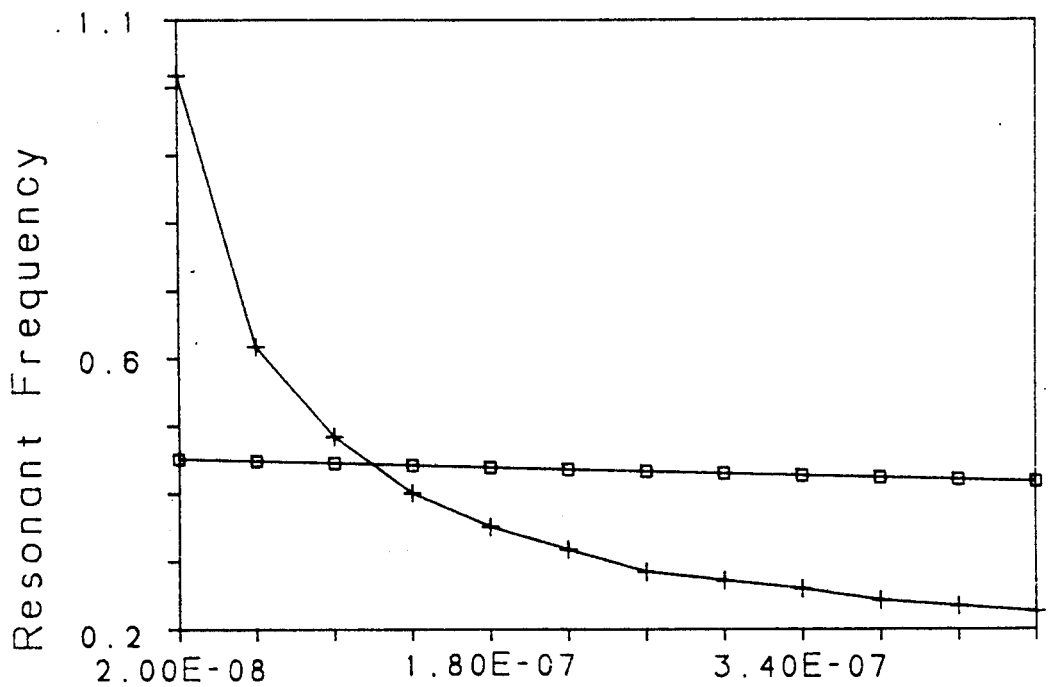
FIG. 14  L12 & L2

APPARATUS FOR ENHANCING BIOINTEGRATION OF BONY AND ENDOPROSTHESIS STRUCTURES

This invention relates to bone healing apparatus and more particularly to an apparatus for promoting bony ingrowth into a porous surface of an endoprosthesis for enhancing biointegration. Biointegration as used herein means a cement free bony integration of the endoprosthesis.

BACKGROUND OF THE INVENTION

Interest in the application of exogenous electrical signals to the problems of tissue growth and repair arises from the discovery and study of electrical signals of endogenous origin, such as piezoelectric type signals associated with mechanical deformation of tissues, and biopotentials associated with the level of tissue viability and cellular metabolic effort. As these electrical signals contain both constant and time dependent components and location dependent components, three exogenous stimulatory signals have been studied in connection with tissue growth and repair. One such signal is the faradic type in which electrodes are placed within the tissue, in or near the location of desired stimulation. A second such signal is a capacitive type signal in which the electrodes are placed externally, on the opposite sides of the limb portion containing the tissue to be stimulated. The third such signal is the inductive type signal in which a coil or pair of coils on a common axis are placed externally so that the coil's axis passes through the limb near to the site to be stimulated.

Faradic systems have characteristic highly focal, diverging radial fields associated with them, produce high local voltage gradients, and generate a wide range of electrode products at cathode and anode. Unlike the other two signals, the use of faradic signals always superimposes the results of tissue trauma on those of electrical stimulation. Capacitive systems have dipole fields, produce relatively modest voltage gradients over large volumes of tissue, and, in the absence of constant bias, produce no electrode products, ionic and electronic current to flow between electrodes. Inductive systems, although producing local voltage gradients similar to those in capacitive systems, produce primary magnetic fields, with potential fields as a secondary effect.

One feature common to the use of the three stimulatory electrical signals is that a similar range of voltage gradients occurs in the vicinity of active osteogenesis.

Fracture healing involves several stages including: inflammation, elaboration (soft callus, hard callus for repair), and remodeling. During inflammation the biopotentials are large and negative, during elaboration (soft callus) the biopotential is falling and by the end (hard callus) the biopotential is nearly normal, and during remodeling the biopotential is normal. Thus, the resistance to the flow of current between the electrodes constitutes a means for measuring the healing process.

Electrical stimulation has been applied to the healing of defects in situations in which bony continuity is still present. Although no device tests are known to exist, acceleration of ingrowth into porous ceramic, porous metallic, and porous polymeric bodies has been demonstrated in canine models. Those persons skilled in the art desiring more information concerning the above mentioned background are referred to an article entitled "Electrical Stimulation of Hard and Soft Tissues in Animal Models" by Jonathan Black, published in Clinics in Plastic Surgery, Vol. 12, No. 2, Apr. 1985, pages 243-257.

A long term endoprosthesis is known in which a relatively large part of the surface, which when implanted makes contact with the bone of the wearer, is provided with coil type electrodes. The electrodes are disposed throughout at least 50 percent of the surface area of bone contact. The electrode spacing decreases in size in accordance with the size of the mechanical area loading on the corresponding part of the contact area. The greater the loading the smaller the spacing. A low frequency power source provides a field strength between about 1.0 to 10 mV/cm. The low frequency alternating voltage, which is produced by a receiving coil can have imposed on it a low direct voltage of a few tenths of a volt. The low voltage is produced by arranging a parallel circuit arrangement of a semi-conductor diode and a capacitor in a lead extending from a receiving coil to the electrode system. The power source is a permanent magnet whose magnetic field is cut by the coils as a hip joint carrying the device moves. Those persons skilled in the art desiring more information about this long term endoprosthesis device are referred to U. S. Pat. No. 4,214,322 issued July 29, 1980.

Thus, it is known that some specific functional link serves to transduce express electrical energies into a bone deposition, formation and cell differentiation. Cells respond and orientate to direct current field patterns under stimulation of cathode placement. In addition a small thin invasive electrical stimulatior device is described in U.S. Pat. No. 4,602,638 issued July 29, 1986 that can be easily implanted and which is operative to both monitor the healing process and to adjust the electrical stimulation in response thereto.

In this device, a pair of insulated leads connect the cathode and anode to an implantable power pack which includes a source of electric power and an insulating encasement. The cathode may be laminal in construction and includes a plurality of spaced-apart frequency modulation (FM) channel monitors embedded within an insulation layer adjacent the conductive electrode forming sheet of material. The FM channel monitors are electrically connected to an FM telemetry component within the power pack for transmitting signals indicative of the electrical characteristics of deposited bone callus, cartilage and soft tissue and therefor, the healing response of a fracture to electrical stimulation. A frequency modulated current regulator may be added to the power pack for adjusting the amperage in response to FM control signals from a remote transmitter. Adjustment of the current flow may be automatically accomplished by providing an implantable computer assisted device responsive to external programming communicated to it by a remote FM transmitter.

Disadvantages of such known systems include the need: to enhance the formation of bone to an implant interface; to control the location of the bone growth to eliminate separation of the bene from the endoprosthesis device resulting from stresses such as those generated by normal body movement; and to provide a less sophisticated means for monitoring the healing process results.

SUMMARY OF THE INVENTION

Accordingly it is an object of the present invention to provide an improved apparatus for the invasive electrical stimulation of bone and soft tissue repair.

Another object of the invention is to provide an endoprosthetic device having an electrical stimulation device for bone fractures and soft tissue and adaptable for healing more types of abnormal bone conditions.

Yet another object of the invention is to provide such an apparatus which includes a novel cathode and anode designed for increased control of the operative surface area.

Still another object of the invention is to provide such an apparatus wherein the electrical stimulation circuit provides a healing progress indicator.

A further object of the invention is to provide a wholly invasive electrical stimulation device for use in an endoprosthesis device.

Briefly stated the invasive apparatus for electrical stimulation of bone abnormalities and soft tissues such as for example, ligaments and tendons includes a circuit suitable for inclusion in an endoprosthesis device adapted for inductive coupling to an exteriorly disposed radio frequency (RF) power supply. The endoprosthesis device includes one or more porous areas whose location(s) is selected at a minimum stress point. An electrode is centrally positioned in the porous area and power is supplied sufficient to promote bony ingrowth only into the porous area. The electrical power supply is a constant current power supply. It has been found that as a bone abnormality heals the resistance to current flow increases. Thus, the change in resistance is reflected in the voltage of the current supply. This voltage when compared to a voltage representative of normal bone conditions indicates both healing progress and when the power supply may be removed.

BRIEF DESCRIPTION OF THE DRAWINGS

Other objects and features of the invention will become more readily understood from the following detailed description when read in conjunction with the accompanying drawings, in which:

FIG. 1 is a diagrammatic view of the induction coupling coils of the electrical stimulating circuits;

FIG. 2 is a schematic diagram of the electrical stimulating circuits;

FIG. 3 shows a partly sectioned elevation of a hip joint prosthesis in accordance with a first embodiment of the invention;

FIG. 4 is a partial sectional view taken along line 4-4 of the shank of the hip joint prosthesis of FIG. 3;

FIGS. 5-14 are graphs showing operational characteristic comparisons between calculated and actual measurements.

Referring now to FIGS. 1 and 2, the electrical stimulating circuit 10 (FIG. 2) comprises an exterior power supply circuit 12 inductively coupled to an interior power distribution circuit 14. The power supply circuit 12 includes a power supply 16 connected to a terminal of a resistor 18 of an inductance-resistance circuit. A coil 20 having a terminal connected to the resistor 18 completes the inductance-resistance circuit, and a mutual inductance coil 22 having terminals connected to coil 20 and to a return lead to the power supply 16 completes the exterior power supply 12. A device 23 (ohmmeter) for measuring load resistance can be connected to the coupling coil for determining the change in load resistance of a constant current regulator for a current cathode or applicator of the interior circuit.

Figure 15:
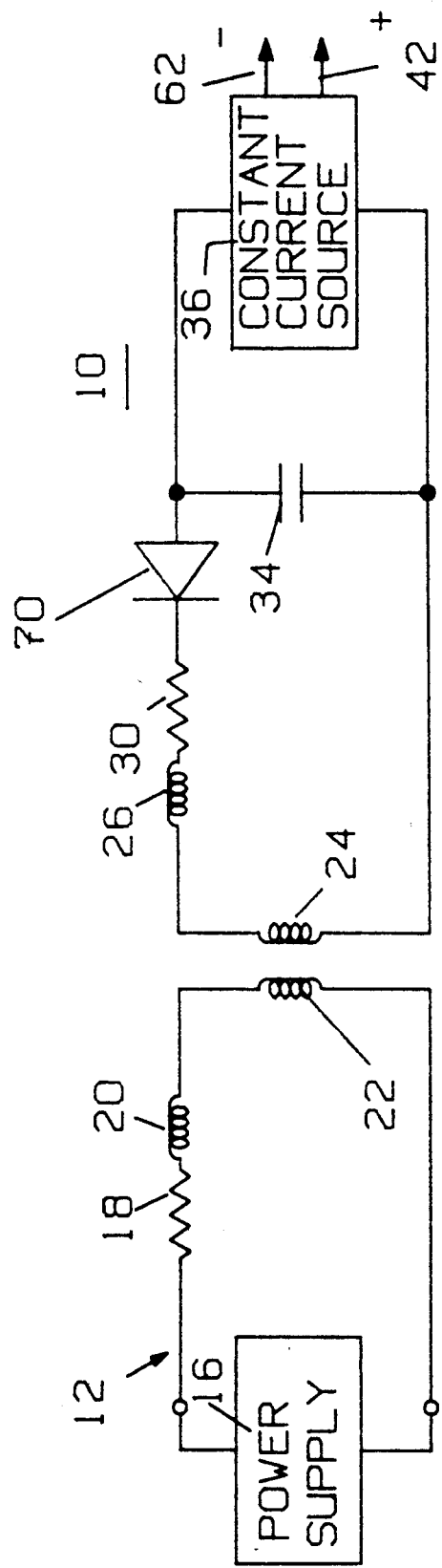
FIGS. 15-16 are views of a second and third embodiment of the electrical stimulating circuit for an endoprosthesis device.

The interior or invasive circuit 14 of the electrical stimulating circuit includes a mutual inductance coil 24 separated a distance "d" (FIG. 1) from the induction coil 22 (FIG. 2) of the exterior circuit 12. Coil 24 has a terminal connected to a coil 26, and coil 26 has a terminal connected to a resistor 30. The resistor 30 has a value including the line and solder joint resistance represented by resistor 32 shown in phantom. The resistor 30 is connected to the junction of a buffer capacitor 34 and a constant current source circuit 36. The capacitor 34 is connected to a return lead to the coupling coil 24. The output of the constant current source circuit 36 is connected to a cathode electrode 62 and electricity passes through the bone structure to an anode electrode 42. The amount of electricity passing through the callus, bone, and soft tissue varies as a function of the callus as it develops into a bony structure. To provide dc a diode 70 (FIG. 15) is inserted between the resistor 30 and junction of capacitor 34 and constant current source. The diode together with the capacitor provides a rectifying circuit for producing a substantially ripple free dc for the electrodes 62 and 42.

The power supply 16 is a Series 500 modular instrument type frequency synthesizer sold by Tecktronix Corporation for producing frequencies between about 0 and 500,000 kHz. The constant current generator 36 is an SN 745ON solid state device sold by Texas Instrument Incorporated for producing a constant current output despite variations in load resistance. The capacitor 34 coacts with the resistor 30 to provide the desired RC time factor for the circuit.

Although inductive coupling is well known, three questions must be answered in determining whether inductive coupling is a feasible method of power transfer for biomedical healing applications. The questions are: (1) can electrical power transfer from a point outside the human body to a point within the body be achieved without direct electrical connection; (2) can the corresponding transferred power be used to provide constant electrical current for biomedical healing applications; and (3) can a device be developed to perform these tasks while meeting constraints on size, power consumption, safety, and cost.

The difficulty in developing a practical working device depends strongly on the particular specifications chosen. The dimensions, efficiency, and frequency specifications each effect the design of the device. Further, there are tradeoffs between them. For example, if the frequency specification is set too low, then it may not be possible to obtain a given efficiency specification.

To determine answers to the above questions a sample device was designed, fabricated, analyzed, and tested to determine if it could perform the tasks of questions 1 and 2 and satisfy the constraints of question 3.

The device specifications were as follows:

| Size: | Dimensions of the coils and circuitry. Diameter of implanted coil not greater than 3.75 mm. Distance between the inductive coils not less than 1.5 cm. |
|---|---|
| Power Consumption: | Efficiency of the coils and circuitry suitable for battery operation. |
| Safety: | Frequency of the magnetic flux between the coils not greater than 500 kHz. |

| Expense: | Final cost of the fabricated device. |
|---|---|

FIG. 1 shows the relationship between the inductive coils. N1 and N2 are the number of turns in the exterior and implanted coils 22 and 24, respectively. The radii of thhe coils are represented by r1 and r2, respectively, and d represents the axial distance between the coils. In the sample construction, the number of coil turns were 10 and 69, respectively, for N1 and N2, the radii r1 and r2 were 1.59 cm and 1.59 mm, respectively, and the wire gauges for the coils 22 and 24 were 18 gauge and 13 gauge, respectively.

Calculated component values for thhe device were first calculated using the formulas of Table 1 for comparison with actual values of the sample device. Table 2 contains the calculated and measured values.

TABLE 1

Equations:

$$(1)\ L_1 = \frac{\mu_0 \pi N_1^2 r_1}{2}$$

$$(2)\ R_1 = 2\pi r_1 N_1\ \text{(Res./length)}$$

$$(3)\ L_2 = \frac{\mu_0 \pi N_2^2 r_2}{2}$$

$$(4)\ R_2 = 2\pi r_2 N_2\ \text{(Res./length)}$$

$$(5)\ L_{12} \approx \frac{\mu_0 \pi}{2} \frac{N_1 N_2 r_1^2 r_2^2}{(d^2 + r_1^2)3/2} \cos\theta$$

Note:
$R_3$ represents additional parasitic resistance not accounted for in the coil resistance equation of $R_2$ $$6.\ \eta = \frac{R_L L_{12}^2 \omega}{(R_L C_L)^2 (L_2^2 R_1 + L_{12}^2 R_2^1)\omega^4 + [R_1 R_L^2 C_L (R'_2{}^2 C_L - 2L_2) + R_1 L_2^2 + R_2' + R_L L_{12}^2]\omega^2 + R_1(R_2' + R_L)^2}$$

$$7.\ \frac{V_o}{V_i} = \frac{\frac{L_{12}}{L_1 L_2 C_L}(j\omega)}{((j\omega) + R_1/L_1)\left[(j\omega)^2 + \left(\frac{R_2}{L_2} + \frac{1}{R_L C_L}\right)(j\omega) + \frac{1}{L_2 C_L}\right]}$$

$$8.\ Y_{in} = \frac{R_L C_L L_2 (j\omega)^2 + [L_2 + R_2 R_L C_L](j\omega) + (R_2 + R_L)}{R_L C_L (L_1 L_2 - L_{12}^2)(j\omega)^3 - (R_1 R_L C_L L_2 + L_1(L_2 + R_2 R_L C_L) - L_{12}^2)\omega^2 + (R_1(L_2 + R_2 R_L C_L) + (R_2 + R_L) L_1)(j\omega) + R_1(R_2 + R_1)}$$

9. Assuming $L_{12}^2 \ll L_1 L_2$ and $R_L \gg R_2$: $Z_{in} = \frac{1}{Y_{in}} = L_1(j\omega + R_1/L_1)$ 10. for maximum $L_{12}$, $r_1 = d$ $$11.\ f_{max} = \frac{1}{2\pi}\left(\frac{R_1(R_2' + R_L)^2}{(R_L C_L)^2(L_2^2 R_L + L_{12}^2 R_2')}\right)^{\frac{1}{4}}$$

(resonant frequency)

When $L_{12} \ll L_2 \sqrt{\frac{R_1}{R_2}} \longrightarrow f_{max} = \frac{1}{2\pi\sqrt{L_2 C_L}}$ 12. for maximum voltage relation, $C_{Lmax} = \frac{L_2}{R_2' R_L}$ 13. $\eta(f_{max} \cdot C_{Lmax}) = \frac{1}{2}$ when $L_{12} \gg L_2 \sqrt{\frac{R_1}{R_L}}$ 14. $\left|\frac{V_o}{V_i}(f_{max} \cdot C_{Lmax})\right| = \frac{L_{12}}{2L_1}\sqrt{\frac{R_L}{R_2'}}$ when $L_1 L_2 \gg L_{12}$ 15. $\frac{V_o}{V_i}\left(\frac{R_1}{2\pi L_1} < f \ll f_{max}\right) = \frac{L_{12}}{L_1}$ Note:
This is a useful relation for measuring mutual inductance.

TABLE 1-continued

16. $Q_v = \dfrac{R_L \sqrt{L_2 C_L}}{L_2 + R_2' R_L C_L}$

17. $Q_v(C_{Lmax}) = \dfrac{1}{2} \sqrt{\dfrac{R_L}{R_2'}}$

TABLE 2

Component Values
Dimensions Used in Calculation $N_1 = 10$   $N_2 = 69$
$r_1 = 1.59$ cm   $r_2 = 1.59$ mm
$d = 1.78$ cm   gauge 1 = 18
gauge 2 = 36

|  | $R_1$ | $L_1$ | $L_{12}$ | $L_2$ | $R_2$ |
|---|---|---|---|---|---|
| Calculated Values | 0.208 Ω | 3.14 μH | 0.043 μH | 14.9 μH | 0.93 Ω |
| Measured Values | 0.219 Ω | 3.30 μH | 0.123 μH | 12.0 μH | 0.75 Ω |

Measurements on the coils were first performed in order to determine the values of the components of the circuit diagram of FIG. 2. The measured results were similar to the calculated values from equations 1-4, but the mutual inductance was more than twice the calculated value using equation 5. The measurement indicates that the inductive coupling between the coils was actually better than predicted by equation 5.

Figure 5:
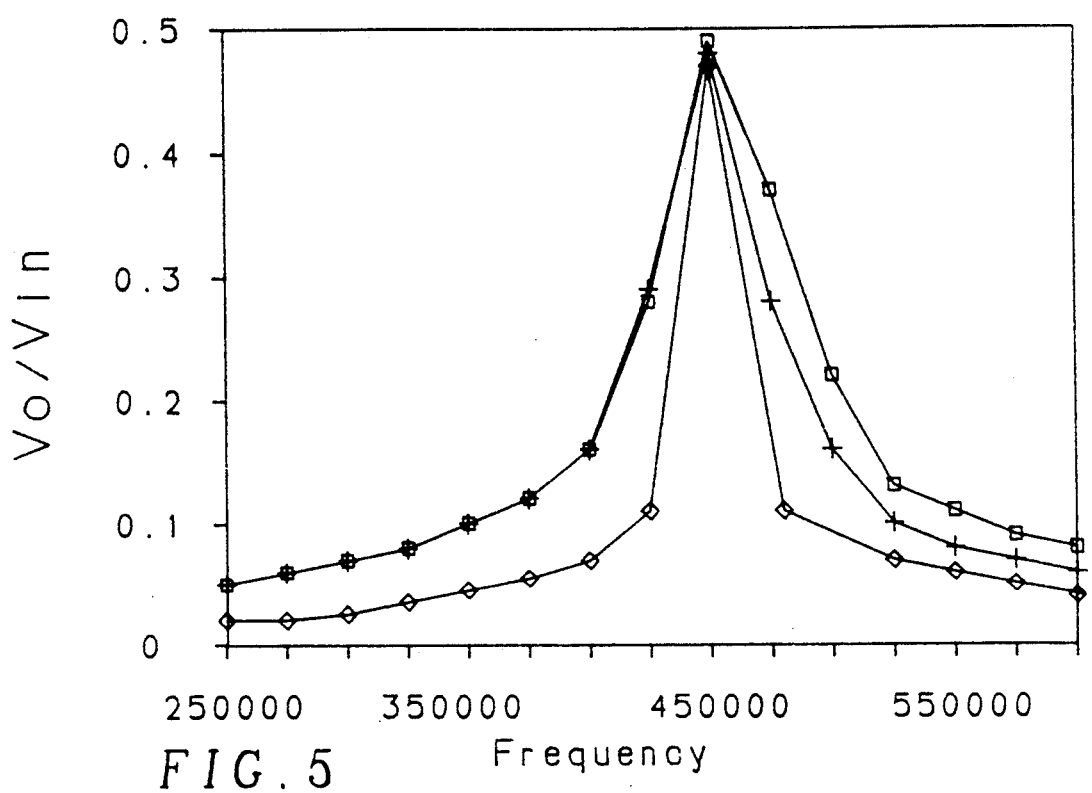

Next measurement was made of the voltage relation $V_0/V_1$ in equation 7. The graph of FIG. 5 shows the measured and corresponding calculated data. This measurement was much lower than predicted using the measured value of mutual inductance. The discrepancy was determined to be the result of inherent resistance in the solder joints, the wires, and the capacitor, CL 34. This is the resistance $R_3$ indicated by resistor 32 as previously mentioned. The graph indicates that the calculation with adjusted values of mutual inductance and resistance closely matches the measured data.

Figure 6:
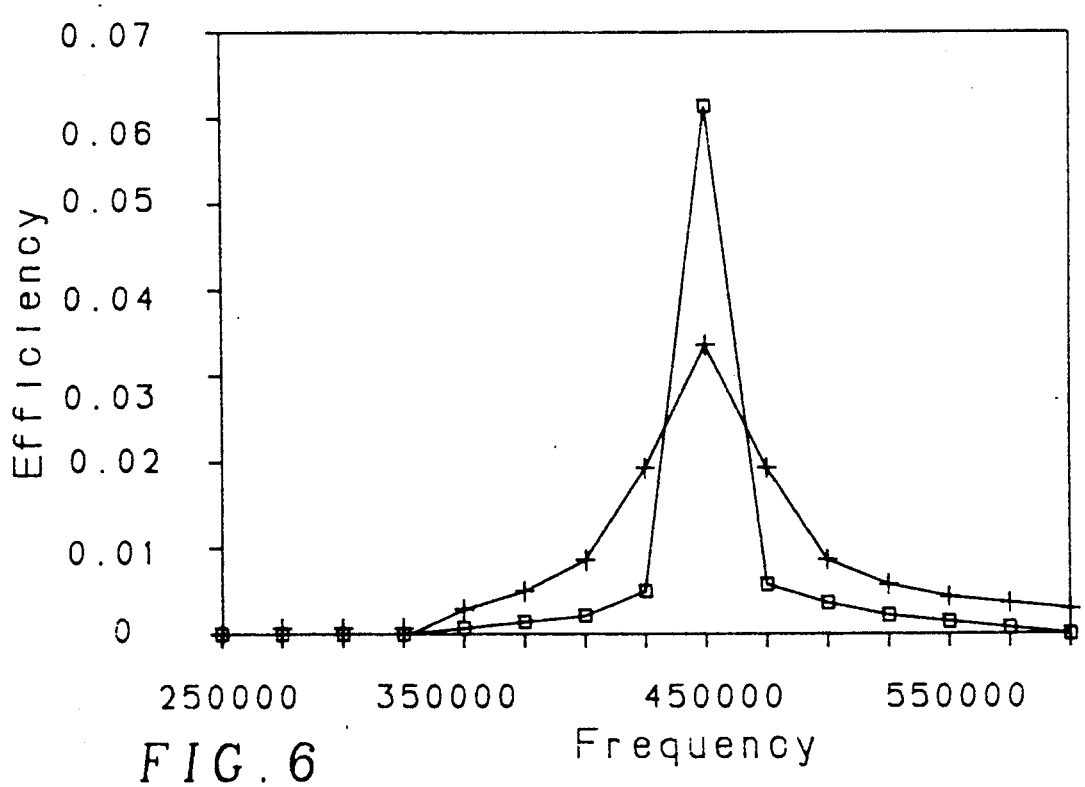
Figure 8:
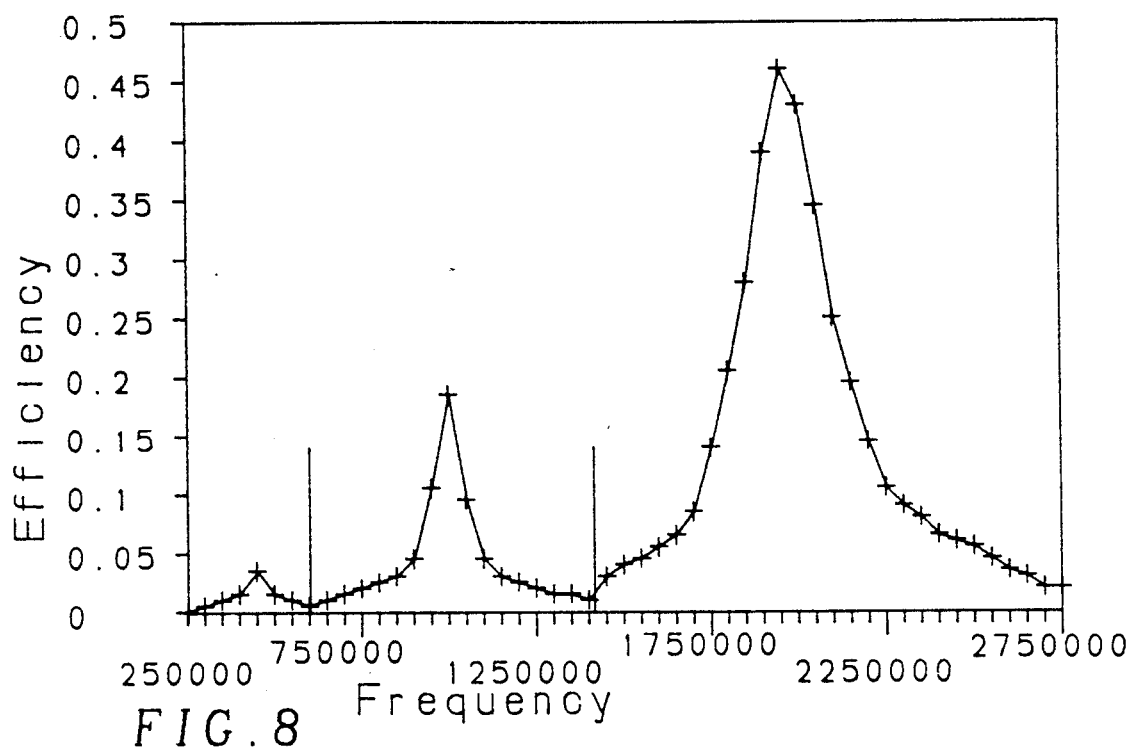
Figure 7:
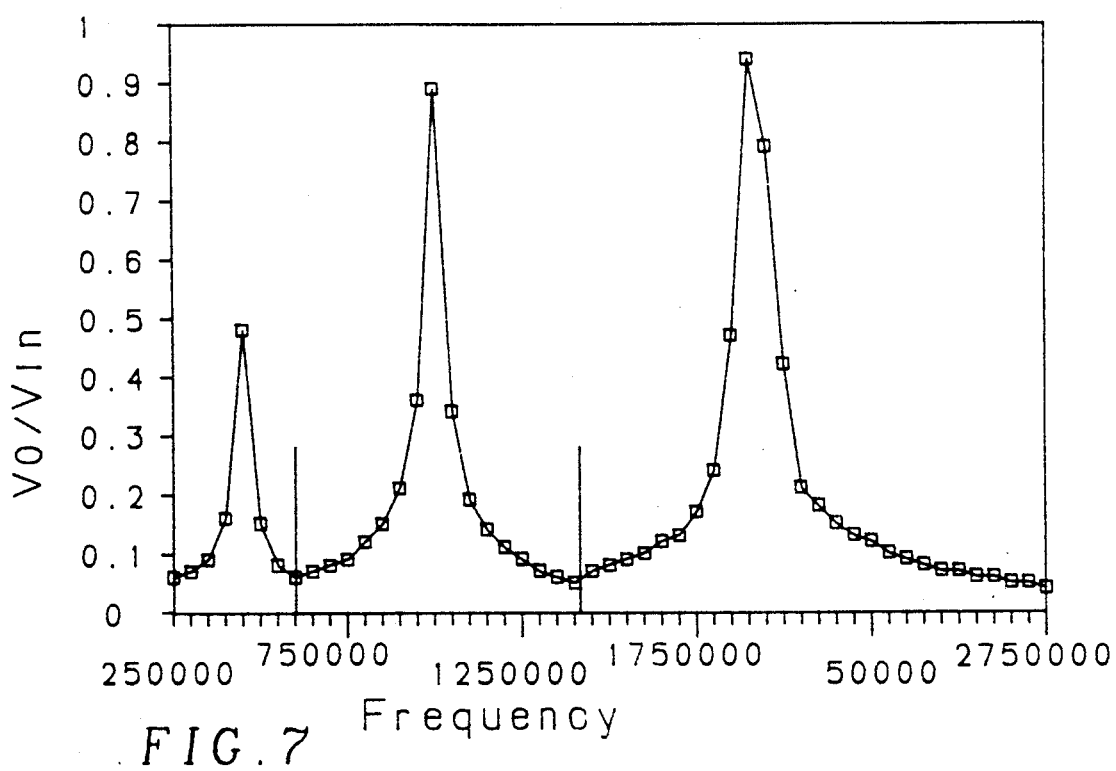
Figure 10:
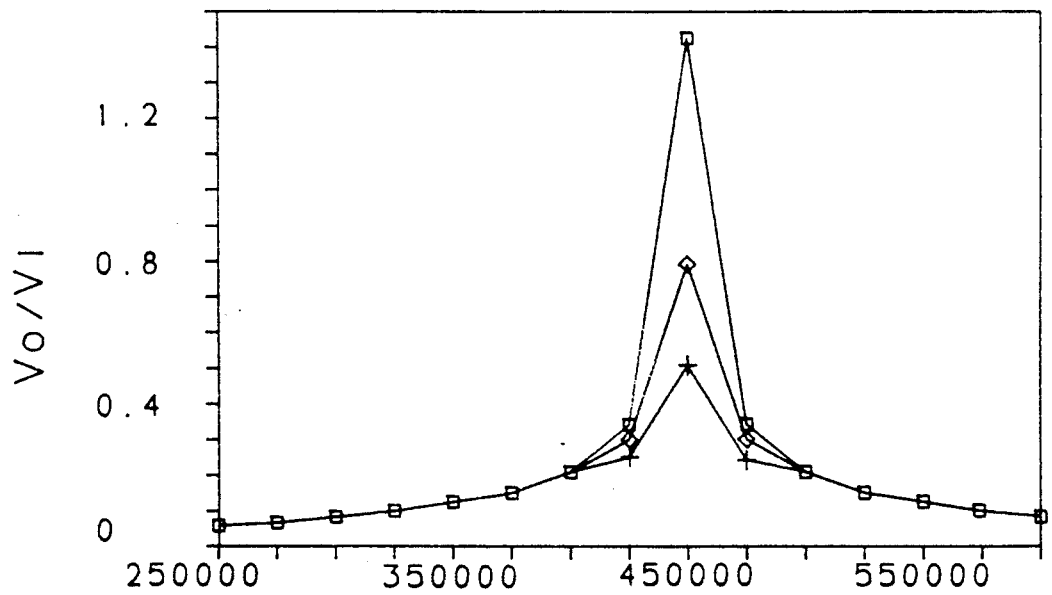
Figure 11:
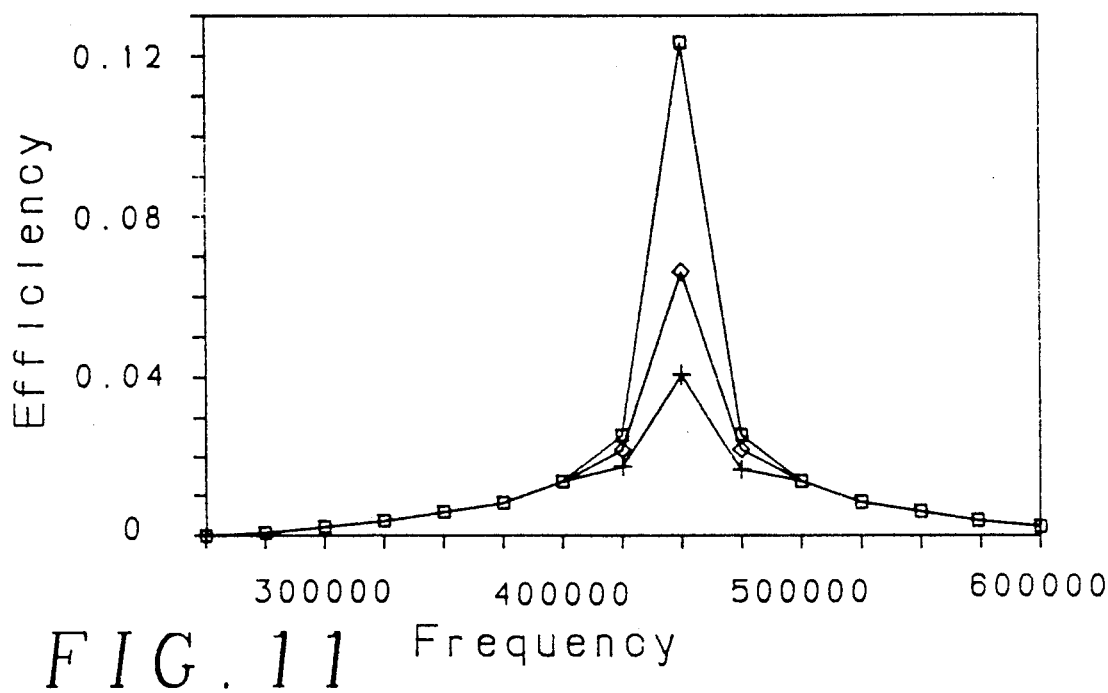
Figure 12:
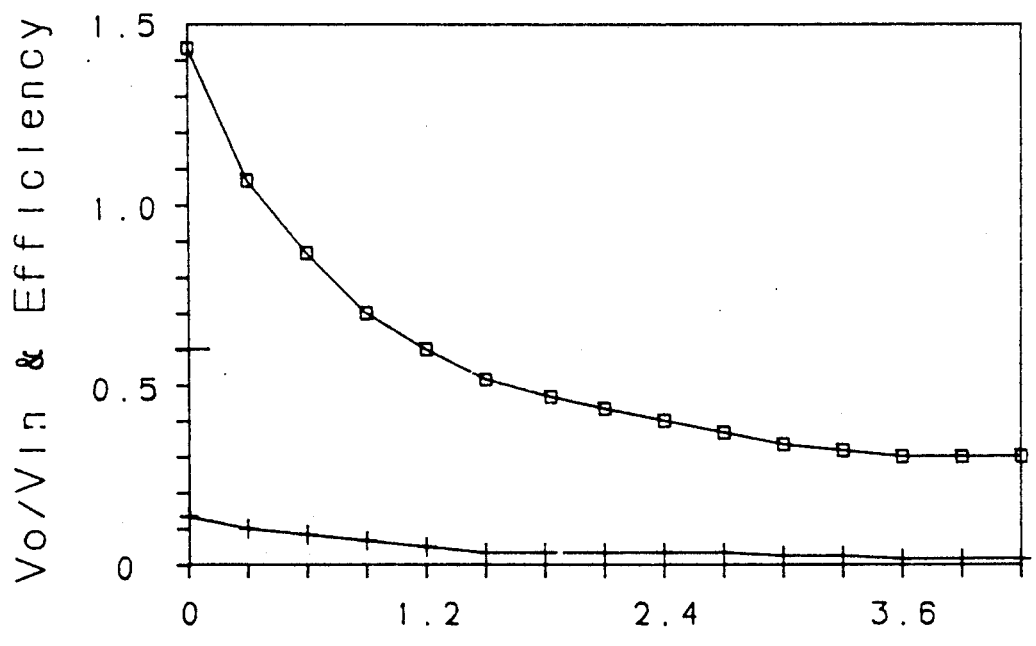

The inherent resistance (indicated as resistor 32) causes an extreme reduction in the peaking of the efficiency and the voltage relation at the resonant frequency as indicated in the graphs of FIGURES 10 and 11. The graph of FIG. 12 shows the dropoff in efficiency and voltage at resonant frequency as the inherent resistance ($R_3$) is varied from 0 to 4.2 ohms. Nevertheless, this effect is not critical as an efficiency of fifty percent can be obtained by using the optimal value of load capacitance, CLmax, and the voltage is applied at the resonant frequency. The difficulty here is that the optimal value of load capacitance decreases with increasing values of the inherent resistance $R_3$ as shown by equation 12. Further, the resonant frequency is inversely related to the value of load capacitance in the circuit as indicated by equation 11. Thus, if the capacitance used in the circuit is decreased towards the value CLmax, then the resonant frequency of the circuit increases as shown in the graphs of FIGS. 6 and 7.

Figure 9:
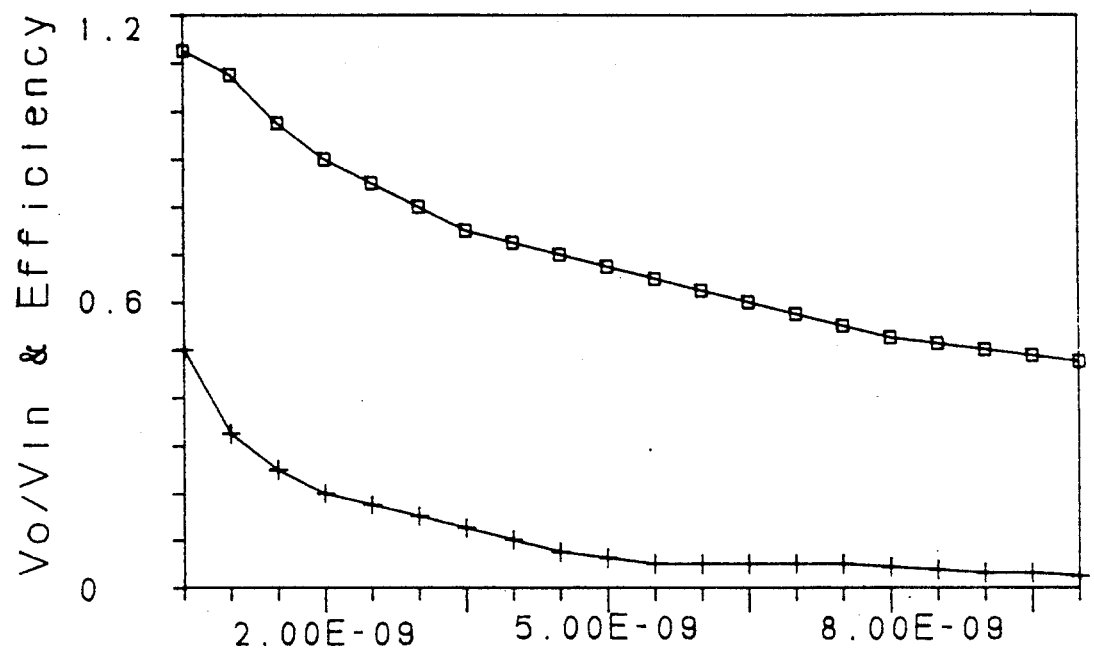

Thus, a tradeoff exists between efficiency and frequency. Operating the coils at lower frequencies than those that would correspond with the value of capacitance, i.e., for example 10.4nF, which is much larger than the optimal value of 0.54nF, results in a much lower efficiency and voltage relation than could be obtained at higher frequencies. The graph of FIG. 9 illustrates the dropoff in voltage and efficiency as the capacitance is increased (which corresponds to a decrease in frequency).

Another tradeoff between frequency and dimensions is also available in this design. A larger number of turns of the inner coil or a larger radrus results in an increased value of self inductance, $L_2$. As shown in equation 11, this results in a decreased resonant frequency. Thus, the design of the coils is based on two tradeoffs. The efficiency can be traded for lower frequency or the dimensions can be traded for lower frequency. By trading efficiency with frequency and then trading frequency for dimensions it is seen that efficiency can be traded for dimensions. Accordingly, each of the three specifications can be traded with one another to arrive at a final design. By taking an approach that dimensions and frequency are inflexible, efficiency is sacrificed.

To obtain a 50% efficiency with the circuit operating at resonance and with optimal capacitance the mutual inductance must be larger than a certain minimum value. This is made clear from equation 13 and the graph of FIG. 13. Thus, a serious design problem exists if the distance between the coils is increased dramatically.

One useful effect of the small mutual inductance between the coils is demonstrated in the graph of FIG. 14; i.e., the resonant frequency is almost unaffected by the mutual inductance. Therefor, the resonant frequency of the inner coil can be measured and the operation of the outer coil set to operate at that frequency.

Figure 16:
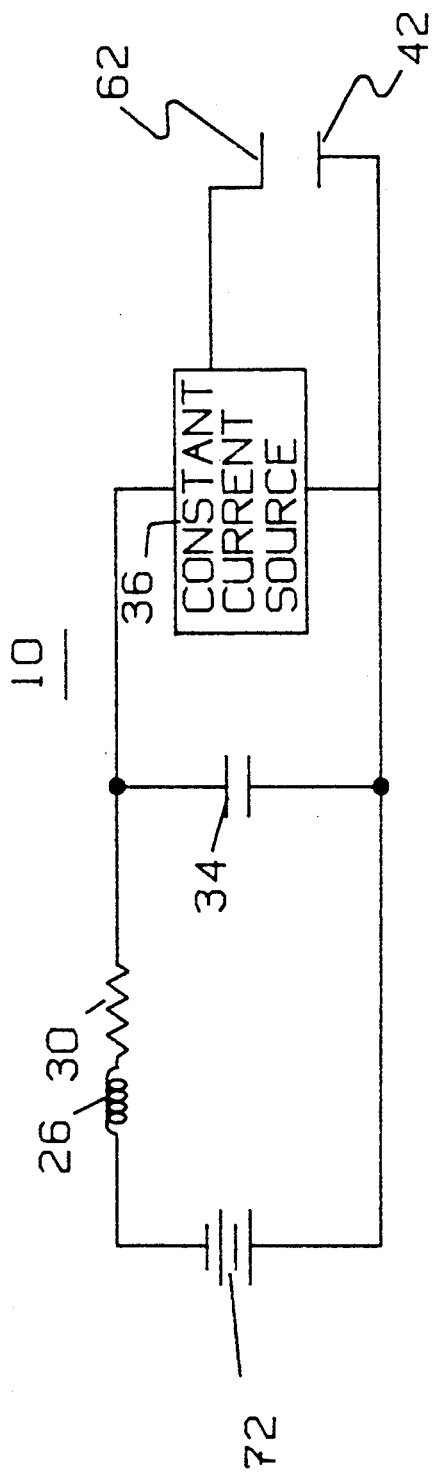

In a third embodiment (FIG. 16), the prosthetic device includes multiple bony growth areas each having a cathode. The power circuit is bedded in the prosthetic device. The power supply is a battery 72 such as, for example, a lithium battery, and a solid state transceiver 74 is connected to the constant current source regulator 36 for transmitting operational information including a continuous signal indicating voltage value and receiving control signals including signals for changing the setting of the current value for the constant current source and for turning the power on and off. The battery power source replaces the external power source, and is incorporated in the constant current source circuitry package.

Referring now to FIG. 3, although the prosthesis device shown and described is a hip bone replacement, it will be appreciated that this is for description purposes only and that other electrical stimulating prosthetic devices can be developed using the principles demonstrated in connection with the hip bone example which will now be described. The outside power supply 16 is packaged in a suitable package 38. The package 38 is equipped with a retaining means 40 for retaining the package on a portion of the body in axial alignment with the induction coil of the inside circuit. A VELCRO(TM) strap has been found suitable for retaining the power pack on a limb.

The invasive circuit includes an anode 42 attached to the exterior surface of the femur bone. The anode 42 consists of a plate of conductive material attached to the femur by a suitable means such as a screw. The anode is for example, a titanium, stainless steel, platinum alloy, or silver/silver chloride plate. The hip bone prosthesis device includes an elongated, tapered shank 44 having a metal ball 46 of a ball and socket joint attached to one end. The cup-shaped socket of the ball and socket joint is a plastic socket 48 formed as the acetabulum of the hip bone. A suitable metal for the metal ball is titanium and a suitable plastic for the socket is polypropylene.

The shank of the hip bone has a shape corresponding to the shape of the femur bone. A threaded well 50 extends downwardly from the top surface of the shank to a point adjacent the center of a porous area 52. The porous area is formed in the shank by plasma deposition, for example. The well 50 contains a power receiving and distribution circuit package 54 comprising the interior power distribution circuit 14. A plug 56 is threadedly attached to the walls of the well. The plug serves to position the power distribution circuit and to close the well. The plug is removable in order to clear the well threads for receiving a threaded rod removal tool for pulling the shank from the femur if required at a later date.

A second well 58 (FIG. 4) centrally located with respect to the porous area 52 is formed to intersect the well 50. The well 58 is electrically insulated, for example, by a Teflon layer 60, and a cathode electrode 62 is pressure fitted in the well with its top surface slightly below the open end of the well. Thus positioned, the soft callus accumulates therein as well as in the pores of the porous area of the shank for bone ingrowth formation. The cathode electrode 62 is connected by wires 64 and 66 extending through wells 58 and 50 with ends connected to the bottom surface of the electrode and opposing ends connected to the power distribution package 54. Although only one pair of electrodes have been described for description purposes, it will be appreciated that additional porous areas will be required on additional sides of the shank and provided with electrodes connected to the power distribution package to properly retain the shank in the femur by means of bone ingrowth.

It will be appreciated that with the cathode electrode electrically insulated from the shank the source of electrical radiation is limited to the electrode, i.e. the shank does not receive electrical power for radiation. Thus, the area of bone growth is limited to the electrical range of the electrode transmitter, which is limited substantially to the area within the peripheral edges of the porous area. The practical result is the elimination of substantial force moments which would result should a cantilever structure be formed by bone growth at the end of the shank opposite the hip bone ball supporting end.

Further, those persons skilled in the art will recognize that other prosthetic devices such as knee joints, shoulder joints, dental implants, ligaments and tendons can be analyzed to determine the proper location for enhancement of the healing process and the electrodes arranged as described above for proper healing in the selected locations.

Finally, those persons skilled in the art will recognize that the power distribution package can be located in one portion of nonunion portions and the anode located in the other portion to reconstruct the union of the member.

Although several embodiments of this invention have been described, it will be apparent to a person skilled in the art that various modifications to the details of construction shown and described may be made without departing from the scope of this invention.

What is claimed is:

1. An invasive prosthesis apparatus for stimulating bone growth and detecting progress of healing the affected bone, comprising:
    External circuit means coupled external to a portion of a human body to be stimulated, comprises:
        An external high frequency current source;
        External coil means for inductive transmission of electrical power; and
        Means for detecting changes in voltage in a selected part of said external circuit means;
    Implanted circuit means implanted within said portion of said human body to be stimulated, comprises:
        Implanted coil means for inductive reception of electrical power from said external coil means;
        Current regulating means for maintaining the current in the implanted circuit means at a predetermined level;
        First and second opposing electrodes operatively connected to said current regulating means, said first and second opposing electrodes being spaced apart and adapted to be positioned adjacent the bone, and
    An implanted prosthesis houses said implanted circuit means, comprises:
        A plurality of porous areas, wherein at least one of said porous areas adapted to receive bony ingrowth, said first electrode being mounted within said porous area;
        Insulating means for electrically isolating said first electrode from said prosthesis; and
        Means for securing said second electrode to said bone spaced away from said prosthesis.

2. The invasive prosthesis apparatus according to claim 1 wherein the first electrode comprises a plurality of cathodic electrodes, at least one cathodic electrode being mounted within each porous area, each cathodic electrode having said insulating means associated therewith.

3. The apparatus according to claim 1 wherein the implanted circuit means further comprise rectifying means for providing a rectified current.

4. The apparatus according to claim 3 wherein the rectifying means comprise a diode and a capacitor.

5. The invasive prosthesis apparatus according to claim 4 wherein the first electrode comprises a plurality of cathodic electrodes, at least one cathodic electrode being mounted within each porous area, each cathodic electrode having said insulating means associated therewith.

6. A method for stimulating bone growth and detecting the progress of healing in affected bone by using an invasive prosthesis device comprises the steps of:
    producing a high frequency electrical flow external to a portion of a human body to be stimulated,
    inductively transmitting power from said high frequency electrical flow to a stimulating circuit implanted within an implanted prosthesis in said human body, receiving said power within said implanted prosthesis, controlling said power in the stimulating circuit at a constant predetermined current level, passing an electrical flow at said constant current level through said portion of the human body to stimulate bone growth, conducting said electrical flow through a cathodic electrode within a porous area on said prosthesis and conducting said electrical flow through an anodic electrode spaced away from said prosthesis, detecting a change in voltage in said high frequency electrical flow caused by a change in electrical resistance of said stimulated portion of said human body, and correlating said detected change in voltage to the progress of healing of the affected bone in said portion of said human body.

7. The method according to claim 6 wherein the step of controlling the power in the stimulating circuit further comprises rectifying thhe electrical flow to direct current flow.

8. The method according to claim 7 wherein the step of rectifying the electrical flow further comprises filtering the direct current flow to reduce ripple.

* * * * *